(12) United States Patent
Huang et al.

(10) Patent No.: US 10,025,077 B2
(45) Date of Patent: Jul. 17, 2018

(54) DEVICE FOR MEASURING SOLUTION CONCENTRATION

(71) Applicant: Chun Kuang Optics Corp., Hsinchu County (TW)

(72) Inventors: Hsin-Chieh Huang, Zhubei (TW); Cheng-Yu Huang, Taoyuan (TW); Shun Wang, Hsinchu County (TW); Shun-Wen Teng, Hsinchu County (TW)

(73) Assignee: CHUN KUANG OPTICS CORP., Hsinchu County (TW)

( * ) Notice: Subject to any disclaimer, the term of this patent is extended or adjusted under 35 U.S.C. 154(b) by 161 days.

(21) Appl. No.: 15/334,462

(22) Filed: Oct. 26, 2016

(65) Prior Publication Data

US 2018/0067288 A1  Mar. 8, 2018

(30) Foreign Application Priority Data

Sep. 5, 2016 (TW) .............................. 105128632 A

(51) Int. Cl.
*G02B 17/00* (2006.01)
*G02B 17/08* (2006.01)
*G01N 21/41* (2006.01)

(52) U.S. Cl.
CPC ....... *G02B 17/086* (2013.01); *G01N 21/4133* (2013.01); *G02B 17/0864* (2013.01); *G01N 2201/062* (2013.01); *G01N 2201/068* (2013.01); *G01N 2201/06113* (2013.01)

(58) Field of Classification Search
CPC ........................ G02B 17/086; G02B 17/0864
See application file for complete search history.

(56) References Cited

U.S. PATENT DOCUMENTS

| | | |
|---|---|---|
| 5,015,091 A | 5/1991 | Suzuki et al. |
| 5,049,742 A | 9/1991 | Hosonuma et al. |
| 9,188,528 B2 | 11/2015 | Bojarski et al. |
| | (Continued) | |

FOREIGN PATENT DOCUMENTS

| | | |
|---|---|---|
| GB | 2089032 A | 6/1982 |
| GB | 2199404 A | 7/1988 |
| | (Continued) | |

*Primary Examiner* — Tri Ton
*Assistant Examiner* — Rebecca C Bryant
(74) *Attorney, Agent, or Firm* — Li & Cai Intellectual Property (USA) Office

(57) ABSTRACT

A device for measuring solution concentration includes housing, a catadioptric structure, an electromagnetic radiation emitter and an electromagnetic radiation detector. The housing is formed with a detecting part for receiving a solution to be detected. The catadioptric structure is received in the housing, and includes a ray entrance portion, a first total internal reflection part, a second total internal reflection part and a ray exit portion. An accommodation part corresponds to the detecting part. The emitter is disposed at one side of the ray entrance portion, and a ray sequentially passes the ray entrance portion, the detecting part, the solution to be detected, and the first total internal reflection part. Then, the ray is totally internally reflected and converged to the second total internal reflection part, and is reflected again. Finally, the ray passes the ray exit portion and is received by the detector.

17 Claims, 13 Drawing Sheets

(56) References Cited

U.S. PATENT DOCUMENTS

| | | | | |
|---|---|---|---|---|
| 2005/0111106 A1* | 5/2005 | Matsumoto | ........... | G02B 7/1805 359/624 |
| 2009/0122300 A1* | 5/2009 | Wu | ................. | G01N 21/4133 356/128 |
| 2011/0249258 A1* | 10/2011 | Rueger | ................. | G01S 3/7803 356/213 |
| 2013/0271756 A1 | 10/2013 | Bojarski et al. | | |

FOREIGN PATENT DOCUMENTS

| | | |
|---|---|---|
| JP | 50-17147 | 6/1975 |
| JP | H01-197632 A | 8/1989 |
| JP | 287050 A | 12/1991 |
| JP | 203567 A | 8/1993 |
| TW | 201506379 A | 2/2015 |

\* cited by examiner

DEVICE FOR MEASURING SOLUTION CONCENTRATION

BACKGROUND

1. Technical Field

The present disclosure relates to a device for measuring solution concentration, in particular, to a device for measuring solution concentration which uses a ray passing a solution to be detected and a catadioptric structure to obtain different refraction indexes, thereby measuring solution concentration.

2. Description of Related Art

There have been many methods to measure solution concentration such as combustion analysis, ion chromatography, titration, and so on. Yet, these conventional analytical methods are costly and time-consuming. In addition, each of the methods has to be operated by skilled personnel, and has potential risks in the process of operation.

Concerning about safety and user-friendliness, the Abbe refractometer is frequently commonly used to measure solution concentration. The reason is that when homogeneous light is transmitted in different substances, its frequency is constant but its wavelength is different. In addition, light having different wavelengths in the same medium such as a lens or air still has different refraction indexes. Thus, when the homogeneous light passes solutions having different concentrations, the wavelength is affected, so that the Abbe refractometer can measure the solution concentration by measuring the refraction index.

The prior art of Patent No.: U.S. Pat. No. 9,188,528B2 has disclosed a sensor for monitoring a medium in which the measurement method is to enable a ray to be totally internally reflected by two times, and then pass a solution to be detected to obtain the solution concentration.

However, neither the methods mentioned above nor the apparatus disclosed in the prior art has an optimal measurement precision.

SUMMARY

The primary purpose of the present disclosure is to provide a device for measuring solution concentration aiming to increase the sensitivity of the measurement of solution concentration.

In addition, the device for measuring solution concentration of the present disclosure is able to avoid bubbles and liquids depositing on the device which would affect the measurement precision.

According to one exemplary embodiment of the present disclosure, a device for measuring solution concentration is provided, including a housing, a catadioptric structure, an electromagnetic radiation emitter, and an electromagnetic radiation detector. The housing has a closed accommodating space formed therein, and a detecting part is formed inwardly on the housing for receiving a solution to be detected. The catadioptric structure is received in the housing, and includes a ray entrance portion, a first total internal reflection part, a second total internal reflection part and a ray exit portion, wherein an accommodation part is formed between the ray entrance portion and the first total internal reflection part, the accommodating part has a shape corresponding to the detecting part, the detecting part is in the accommodating part, and the ray exit portion has a ray exit face. The electromagnetic radiation emitter is disposed at one side of the ray entrance portion, a ray emitted by the electromagnetic radiation emitter sequentially passes the ray entrance portion, the detecting part, the solution to be detected and the first total internal reflection part, and then the ray is totally internally reflected and converged to the second total internal reflection part and totally internally reflected again to pass the ray exit portion. The electromagnetic radiation detector is disposed at one side of the ray exit portion for receiving the ray from the ray exit portion. The ray exit face faces the electromagnetic radiation detector.

In a preferred embodiment, the device for measuring solution concentration further includes a notch formed between the first total internal reflection part and the second total internal reflection part. The first total internal reflection part includes a first exit face, the second total internal reflection part includes a second entrance face, and the first exit face and the second entrance face are not parallel to each other and define the notch together.

According to another exemplary embodiment of the present disclosure, a device for measuring solution concentration is provided which includes a housing having a closed accommodating space formed therein, a detecting part formed inwardly on the housing for receiving a solution to be detected, and a catadioptric structure received in the housing. The catadioptric structure includes a ray entrance portion, a first total internal reflection part, a second total internal reflection part and a ray exit portion, wherein an accommodation part is formed between the ray entrance portion and the first total internal reflection part, the accommodating part has a shape corresponding to the detecting part, the detecting part is in the accommodating part, wherein the detecting part has a shape of a ditch and is parallel to a direction of gravity, and has two open ends. The ray exit portion has a ray exit face. An electromagnetic radiation emitter is disposed at one side of the ray entrance portion, a ray emitted by the electromagnetic radiation emitter sequentially passes the ray entrance portion, the detecting part, the solution to be detected and the first total internal reflection part, and then the ray is totally internally reflected and converged to the second total internal reflection part and totally internally reflected again to pass the ray exit portion. An electromagnetic radiation detector is disposed at one side of the ray exit portion for receiving the ray from the ray exit portion. The ray exit face faces the electromagnetic radiation detector.

In a preferred embodiment, the second total internal reflection part further includes a second total internal reflection face which is a non-planar surface and a free-form surface.

To sum up, the device for measuring solution concentration provided by the present disclosure is to enable a ray emitted by the electromagnetic radiation emitter to produce an angle deflection before entering a solution to be detected, and when in the catadioptric structure, the ray is totally internally reflected by two times, and is also refracted by two times by the notch to magnify the deflection angle, wherein the present disclosure can magnify the deflection angle by several times, thereby enhancing the sensibility. In addition, the second total internal reflection surface may have a convex lens-like shape or a free-form surface formed by connecting a plurality of micro-planes used to magnify the deflection angle. The detecting part of the present disclosure has a shape of a ditch and is parallel to a direction of gravity, and has two open ends, thereby enabling the solution to be detected in a liquid container to freely pass the detecting part without being deposited on the housing to avoid covering the housing, so that the accuracy of measuring solution concentration is not affected.

In order to further understand the techniques, means and effects of the present disclosure, the following detailed descriptions and appended drawings are hereby referred to, such that, and through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

Figure 1:
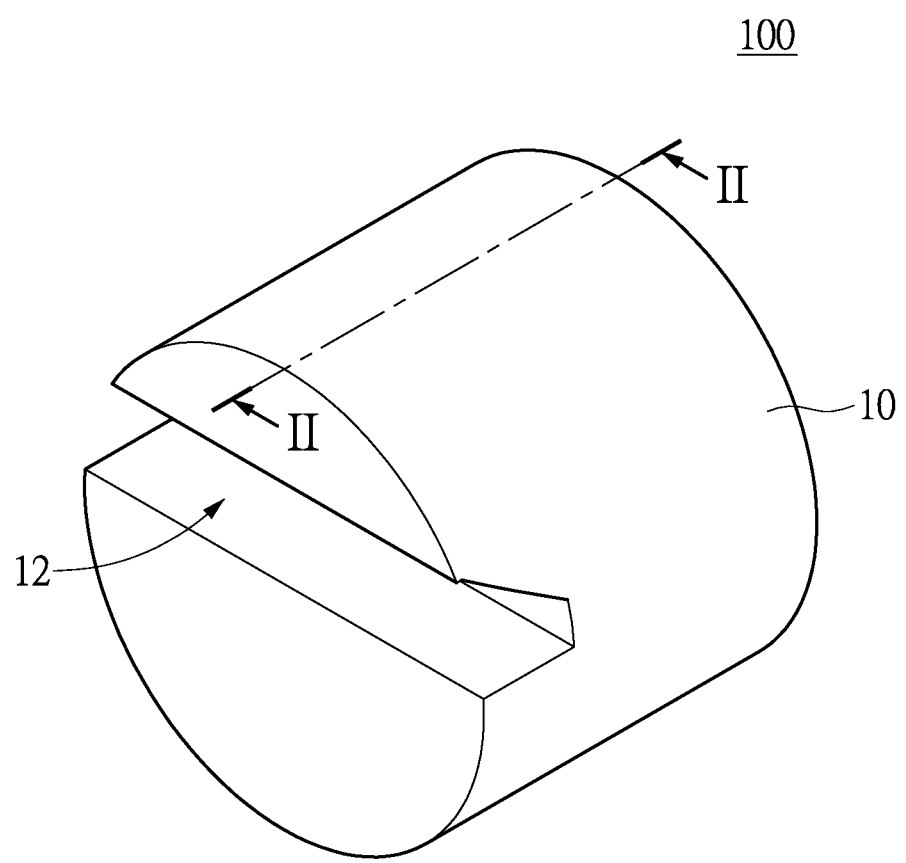
FIG. 1 is a three-dimensional diagram of the device for measuring solution concentration of the present disclosure.

Reference will now be made in detail to the exemplary embodiments of the present disclosure, examples of which are illustrated in the accompanying drawings. Wherever possible, the same reference numbers are used in the drawings and the description to refer to the same or like parts.

Figure 2:
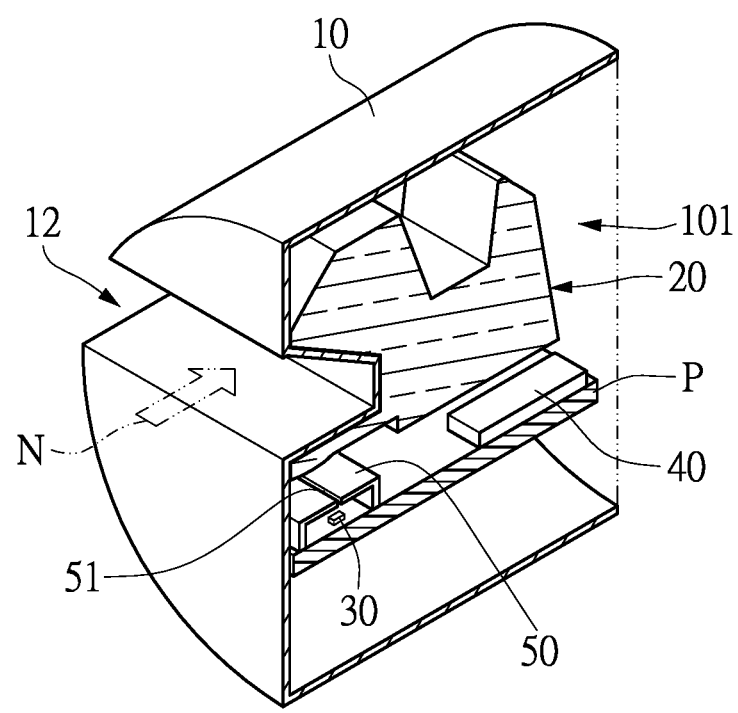
FIG. 2 is a three-dimensional sectional view of the device for measuring solution concentration of the present disclosure.

Please refer to FIG. 1 and FIG. 2, which are respectively a three-dimensional diagram of the device for measuring solution concentration of the present disclosure and a three-dimensional sectional view illustrating the device for measuring solution concentration of the present disclosure along the line II-II shown in FIG. 1. A device for measuring solution concentration 100 is provided, including a housing 10, a catadioptric structure 20 received in the housing 10, an electromagnetic radiation emitter 30 and an electromagnetic radiation detector 40. The electromagnetic radiation may be X-ray, ultraviolet light, visible ray, infrared ray, far-infrared ray, and so on.

As shown in FIG. 2, the device for measuring solution concentration 100 further includes a circuit board P. Because of the disposition of the catadioptric structure 20, the electromagnetic radiation emitter 30 and the electromagnetic radiation detector 40 are disposed at the same side and on the same plane of the circuit board P. Such a structure is easy to assemble. In the present embodiment, a ray shield 50 is provided between the electromagnetic radiation emitter 30 and the catadioptric structure 20.

In the present embodiment, the housing 10 is substantially formed as a cylinder, and a closed accommodating space 101 is formed therein. Here, the shape of the housing 10 of the present disclosure is not limited thereto, and it can be a rectangular shape or other shapes. A detecting part 12 is formed inwardly on the housing 10 for receiving a solution to be detected N. The solution may be urea or other liquids. The housing 10 is preferably made of a ray-transmittable material.

Figure 3:
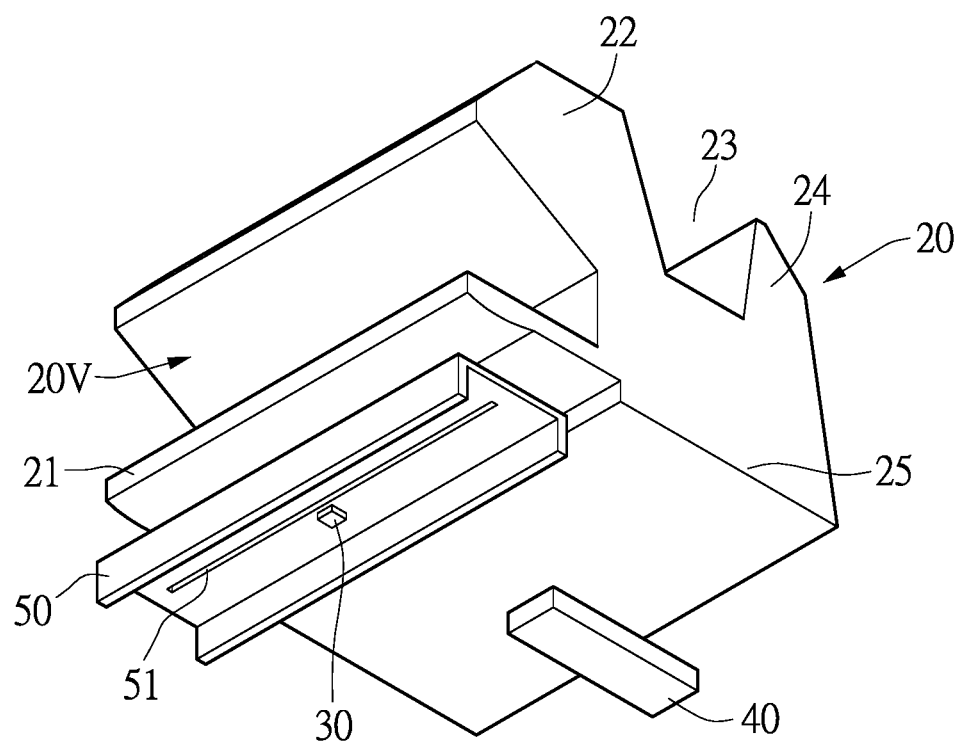
FIG. 3 is a three-dimensional diagram of the device for measuring solution concentration of the present disclosure of which the housing is removed.
Figure 4:
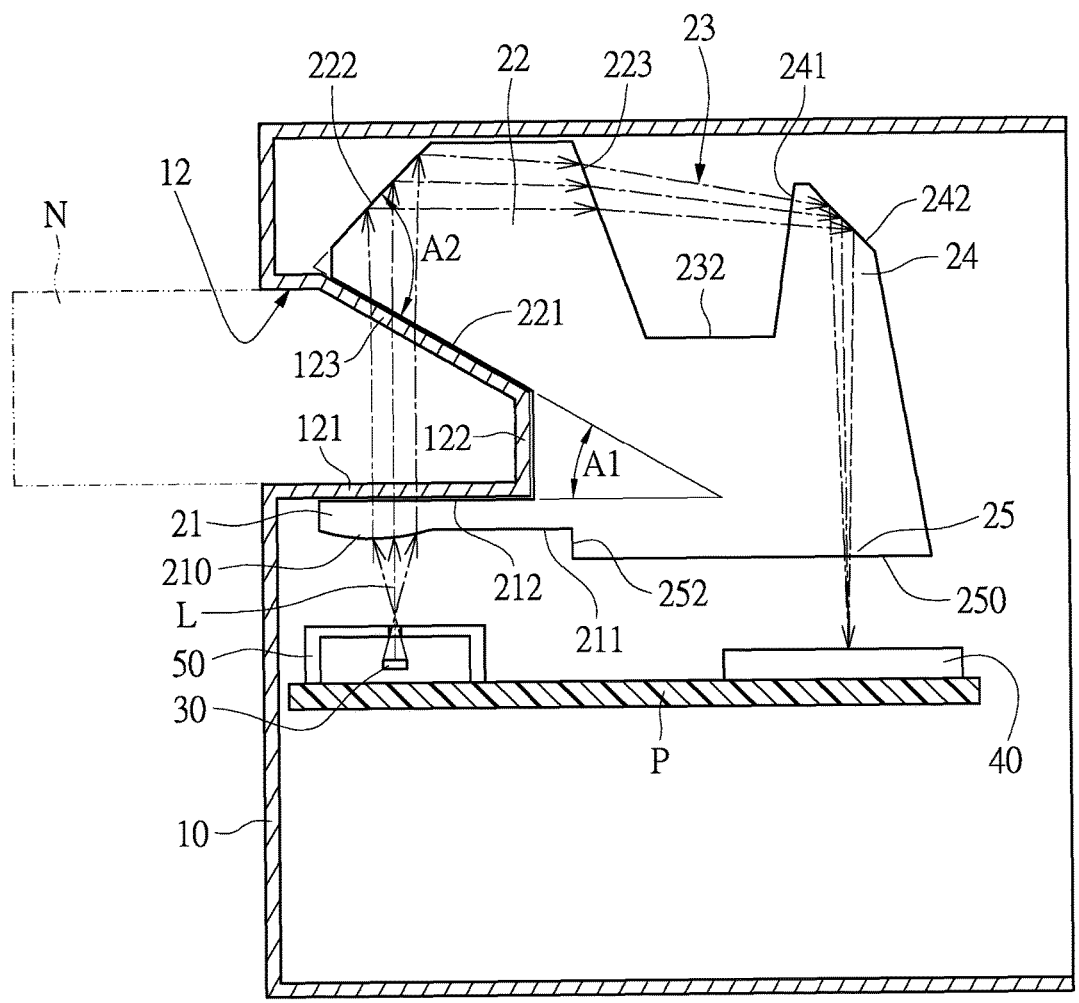
FIG. 4 is a sectional view of the device for measuring solution concentration of the present disclosure.

Please refer to FIG. 3 and FIG. 4, which are respectively a three-dimensional diagram of the device for measuring solution concentration of the present disclosure of which the housing is removed and a sectional view of the device for measuring solution concentration of the present disclosure. The catadioptric structure 20 is received in the housing 10. In the present embodiment, the catadioptric structure 20 has the same longitudinal profile, and includes a ray entrance portion 21, a first total internal reflection part 22, a second total internal reflection part 24 and a ray exit portion 25, wherein an accommodation part 20V is formed between the ray entrance portion 21 and the first total internal reflection part 22, the accommodating space 20V has a shape corresponding to the detecting part 12, and the detecting part 12 is disposed in the accommodating part 20V. A face of the ray entrance portion 21 facing the electromagnetic radiation emitter 30 is a convex lens-like shape and has a ray-converging part 210, wherein the convex lens-like shape may be a cylindrical or a spherical shape. The ray-converging part 210 is beneficial to ray convergence. A top surface 212 of the ray entrance portion 21 facing the detecting part 12 is a plane.

As shown in FIG. 4, the electromagnetic radiation emitter 30 is disposed at one side of the ray entrance portion 21. A ray L emitted by the electromagnetic radiation emitter 30 sequentially passes the ray entrance portion 21, the detecting part 12, the solution to be detected N and the first total internal reflection part 22, then is refracted by two times by a notch 23, and is totally internally reflected and converged to the second total internal reflection part 24 and totally internally reflected again to pass the ray exit portion 25.

The electromagnetic radiation emitter 30 may be a laser or a light emitting diode (LED). The ray shield 50 is disposed between the electromagnetic radiation emitter 30 and the ray entrance portion 21 and used to shield from other electromagnetic radiation to avoid interference. In addition, a slit 51 is formed on the ray shield 50 and used to guide the ray L emitted by the electromagnetic radiation emitter 30 to enter the ray entrance portion 21 of the catadioptric structure 20 according to the direction of the slit 51.

The electromagnetic radiation detector 40 is disposed at one side of the ray exit portion 25 for receiving the ray L from the ray exit portion 25. The electromagnetic radiation detector 40 may be a photoelectric detector, a photoelectric diode, and so on.

The detecting part 12 of the housing 10 includes a first ray-transmittable board 121, a second ray-transmittable board 123, and a connecting board 122 for connecting the first ray-transmittable board 121 and the second ray-transmittable board 123, wherein the first ray-transmittable board 121 horizontally attaches to a surface of the ray entrance portion 21 and is parallel to the circuit board P, and the second ray-transmittable board 123 is inclined to the circuit board P. As shown in FIG. 4, an acute angle which is denoted as the first included angle A1 is formed between the first ray-transmittable board 121 and the second ray-transmittable board 123.

The first total internal reflection part 22 has a first entrance face 221 and a first total internal reflection face 222, wherein the first entrance face 221 attaches to the second ray-transmittable board 123, and an acute angle which is denoted as the second included angle A2 is formed between the first entrance face 221 and the first total internal reflection face 222. The first total internal reflection face 222 of the first total internal reflection part 22 may be a plane or a free-form surface, and is not limited thereto.

In the present embodiment, the device for measuring solution concentration 100 further includes a notch 23 formed between the first total internal reflection part 22 and the second total internal reflection part 24. The first total internal reflection part 22 includes a first exit face 223, the second total internal reflection part 24 includes a second entrance face 241, and the first exit face 223 and the second entrance face 241 are not parallel and define the notch 23 together. The second entrance face 241 of the second total internal reflection part 24 may be a plane.

Please refer to FIG. 4 again. In the present embodiment, the ray L passes the first ray-transmittable board 121 of the housing 10 through the ray entrance portion 21, and then substantially perpendicularly enters the solution to be detected N. Then, the ray L passes the second ray-transmittable board 123 of the housing 10 to enter the first total internal reflection part 22 of the catadioptric structure 20. After deflecting, the ray L is totally internally reflected by the first total internal reflection face 222, wherein the ray L totally internally reflected by the first total internal reflection face 222 is almost parallel to the circuit board P. Then, the ray L enters the notch 23 and is refracted by two times by the notch 23. After that, the ray L enters the second total internal reflection part 24 of the catadioptric structure 20. Finally, after deflecting four times, the ray L passes a ray exit face 250 of the ray exit portion 25 and is received by the electromagnetic radiation detector 40. The ray exit face 250 is opposite to the electromagnetic radiation detector 40, and the ray exit face 250 and the electromagnetic radiation detector 40 are substantially parallel to each other.

The catadioptric structure 20, the solution to be detected N and the notch 23 have their respective refraction indexes, causing the ray L to be deflected several times when passing through them. Particularly, when the solution to be detected N is in different concentrations, the refraction index is also different. Thus, the electromagnetic radiation detector 40 can detect positions of the ray L caused by the numerous refractions and reflections to determine the concentration of the solution to be detected N more precisely.

Figure 5:
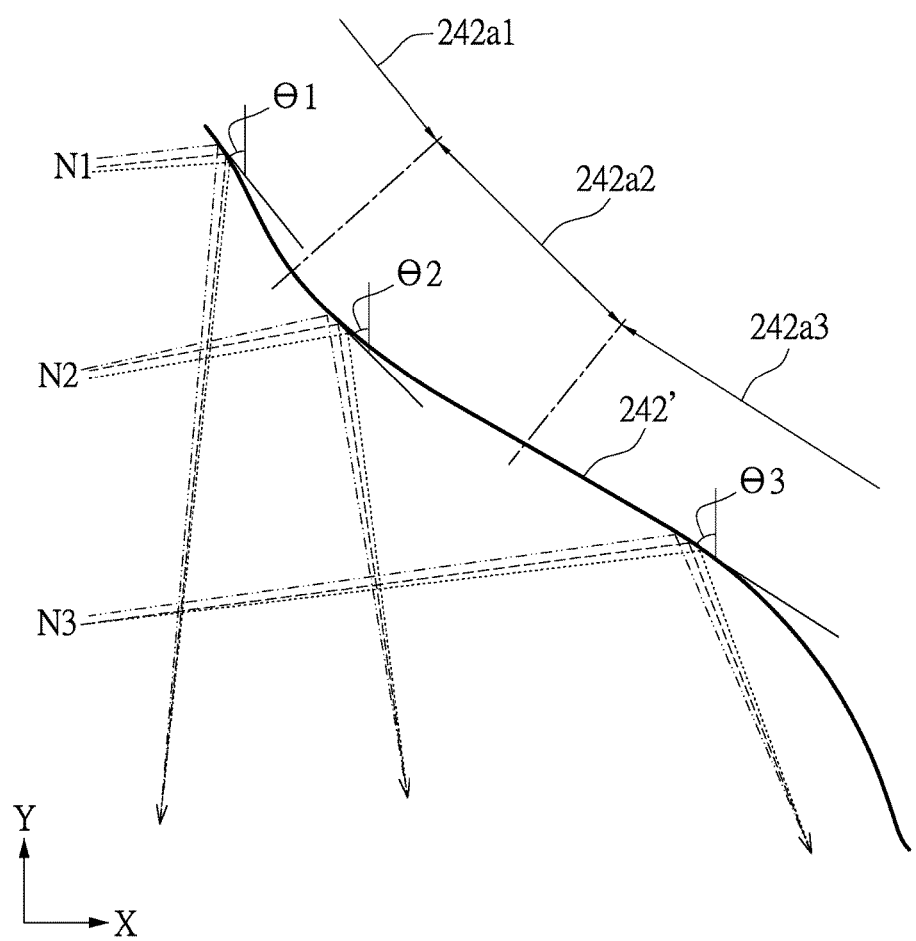
FIG. 5 is a three-dimensional enlarged view of the second embodiment of the second total internal reflection face of FIG. 4.

Please refer to FIG. 5 which is a three-dimensional enlarged view of the second embodiment of the second total internal reflection face shown in FIG. 4. In the present embodiment, the characteristic of the device for measuring solution concentration is that the second total internal reflection face 242' of the second total internal reflection part 24 is not a plane but a free-form surface such as a S-shaped surface or a free-form surface formed by connecting a plurality of micro-planes, thereby forming reflection areas having different total reflection angles. The advantage of the non-planar structure is that different refraction indexes cause the ray L to have different deflection angles, so that when leaving the notch 23 and entering the second total internal reflection part 24, the ray L is deflected and converged at different positions of the second total internal reflection part 24. When the ray L at different angles is totally internally reflected by the second total internal reflection face 242', the deflected angle is magnified to enable the electromagnetic radiation detector 40 to read the data more easily.

More specifically, as shown in FIG. 5, the second total internal reflection face 242' which is a free-form surface has a plurality of reflection sections, and each of the reflection sections has a reflecting curved surface with a gradient. In the present embodiment, there are three reflection sections provided. The second total internal reflection face 242' has an upper reflection section 242a1, a main reflection section 242a2 and a lower reflection section 242a3, wherein the main reflection section 242a2 is between the upper reflection section 242a1 and the lower reflection section 242a3.

The main reflection section 242a2, the upper reflection section 242a1 and the lower reflection section 242a3 have different reflection gradients. When the present disclosure is used to measure solutions, e.g. N1, N2, and N3 having their respective refraction indexes, the dotted lines shown in FIG. 5 are used to respectively illustrate the path of the ray for N1, N2 and N3. When passing the second total internal reflection part 24, the ray in the three solutions having their respective refraction indexes is distributed on different sections of the second total internal reflection face 242'.

Please refer to FIG. 5 again. Regarding the relationship of the reflection gradient among the three reflection sections of the second total internal reflection face 242', it is denoted as follows: the upper reflection section 242a1>the main reflection section 242a2>the lower reflection section 242a3. A first included angle $\theta 1$, a second included angle $\theta 2$ and a third included angle $\theta 3$ are respectively formed between the tangent lines of the three sections and the imaginary line perpendicular to the ray exit face 250, wherein the first included angle $\theta 1$<the second included angle $\theta 2$<the third included angle $\theta 3$. The reflection section which is adjacent to the notch 23 has the greater refraction gradient than the remaining sections, so that the ray passing the solution having the refraction index N1 is directed to left side of FIG. 5 when being reflected by the upper reflection section 242a1. The reflection section which is far from the notch 23 has the smaller refraction gradient than the remaining sections, so that the ray passing the solution having the refraction index N3 is directed to right side of FIG. 5 when being reflected by the lower reflection section 242a3. The ray respectively passing through the three solutions having different refraction indexes has a fanlike deflection distributing at different positions of the electromagnetic radiation detector 40. Thus, the present disclosure can read the data more easily and precisely to increase the sensitivity to the measurement according to the measurement method.

Figure 7:
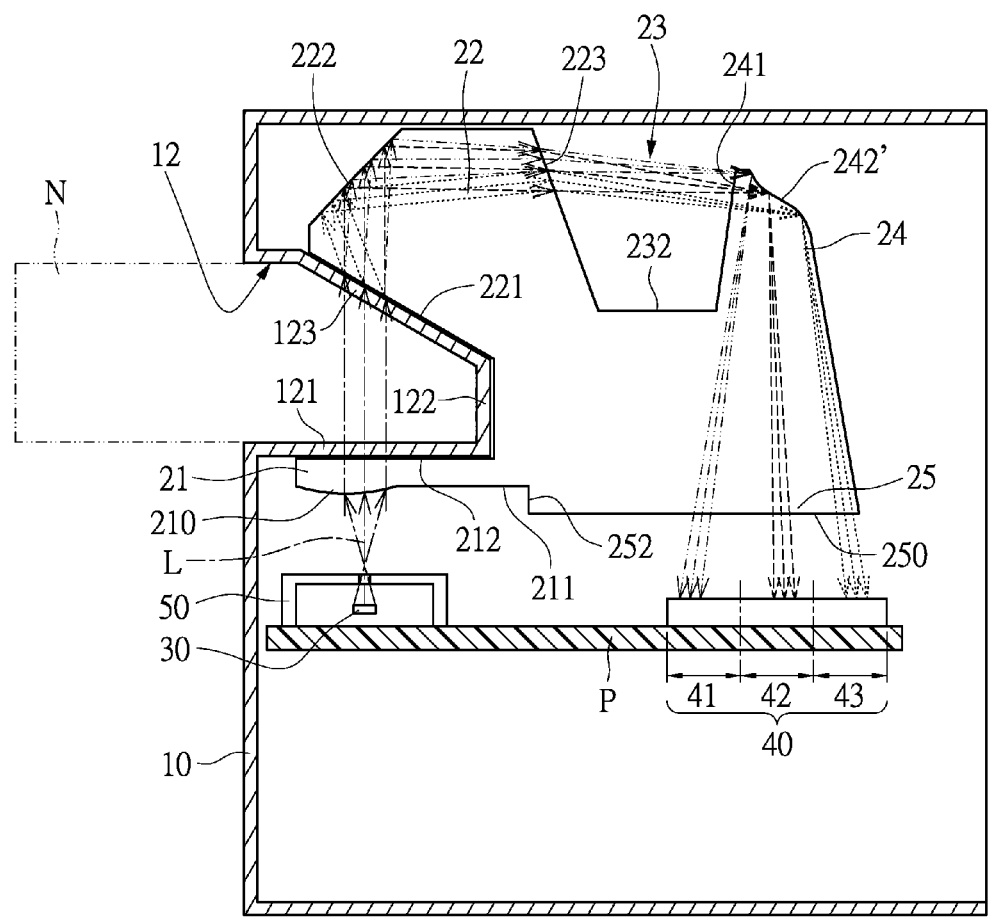
FIG. 7 is a schematic diagram illustrating optical paths of solution having three refraction indexes detected by the device for measuring solution concentration of the present disclosure.

Please refer to FIG. 7 which is a schematic diagram illustrating optical paths of the three solutions having different refraction indexes detected by the device for measuring solution concentration of the present disclosure. The upper reflection section 242a1 reflects the ray to a first area 41 of the electromagnetic radiation detector 40, the main reflection section 242a2 reflects the ray to a second area 42 of the electromagnetic radiation detector 40, and the lower reflection section 242a3 reflects the ray to a third area 43 of the electromagnetic radiation detector 40, wherein the second area 42 is between the first area 41 and the third area 43.

Figure 6:
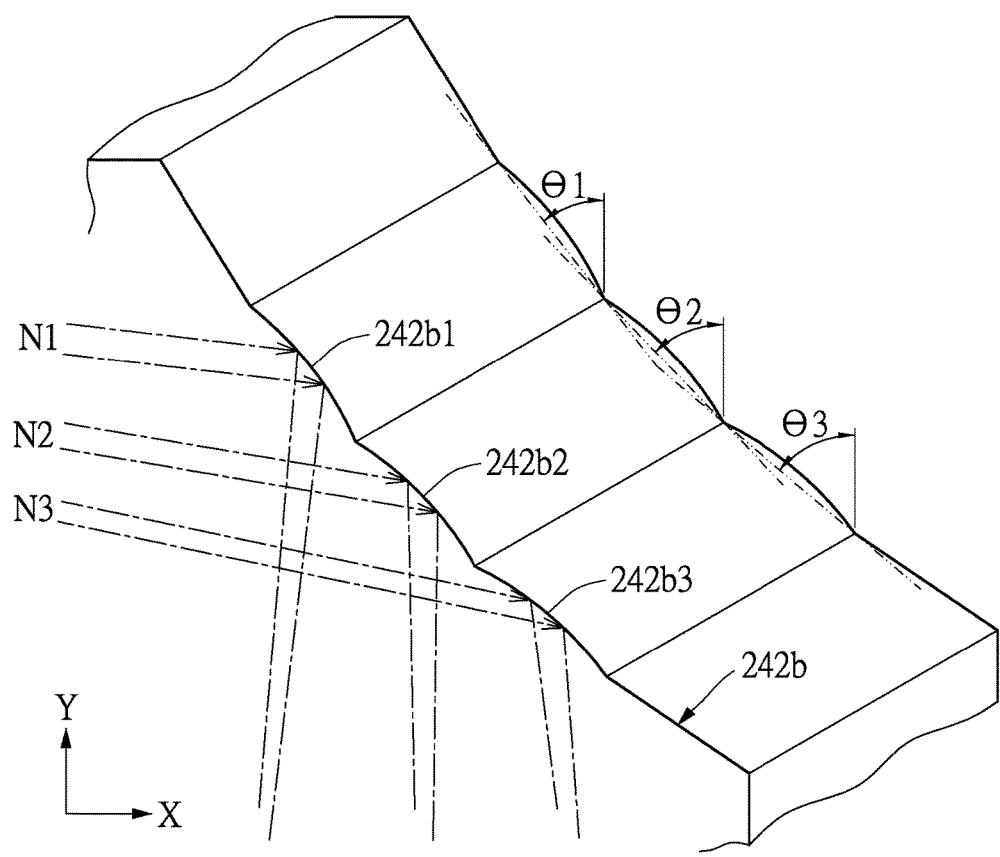
FIG. 6 is a three-dimensional enlarged view of the third embodiment of the second total internal reflection face of FIG. 4.

Please refer to FIG. 6 which is a three-dimensional enlarged view of the third embodiment of the second total internal reflection face shown in FIG. 4. In the present embodiment, a second total internal reflection face 242b has a discontinuous reflection surface. There are three reflection surfaces used in the example, which are a first reflection surface 242b1, a second reflection surface 242b2 and a third reflection surface 242b3, wherein the second reflection surface 242b2 is between the first reflection surface 242b1 and the third reflection surface 242b3. Regarding the gradient of the three reflection surfaces, it is denoted as follows: the first reflection surface 242b1>the second reflection surface 242b2>the third reflection surface 242b3. In addition, a first included angle $\theta 1$, a second included angle $\theta 2$ and a third included angle $\theta 3$ are respectively formed between the first reflection surface 242b1, the second reflection surface 242b2 and the third reflection surface 242b3 and the imaginary line perpendicular to the ray exit face 250, wherein the first included angle $\theta 1$<the second included angle $\theta 2$<the third included angle $\theta 3$. The present embodiment has the similar function as described in the former embodiment.

To be precise, the ray passing the solution having the refraction index N1 is reflected by the first reflection surface 242b1, and as the first reflection surface 242b1 has the greater gradient than the remaining surfaces, the ray is reflected and converged at the left side of FIG. 6. The ray passing the solution having the refraction index N3 is reflected by the third reflection surface 242b3, and as the third reflection surface 242b3 has the smaller gradient than the remaining surfaces, the ray is reflected and converged at the right side of FIG. 6. The ray respectively passing the three solutions having the refraction index N1, N2, N3 has a fanlike deflection distributing at different positions of the electromagnetic radiation detector 40. Thus, the present disclosure can read the data more easily and precisely to increase the sensitivity to the measurement according to the measurement method mentioned above.

The difference between the present embodiment and the former embodiment is that the first reflection surface 242b1, the second reflection surface 242b2 and the third reflection surface 242b3 of the present embodiment all have an arc surface, and each of the arc surfaces is beneficial to focus light. As shown in FIG. 6, the ray which respectively passes through the three solutions having different refraction indexes is converged by the three reflection surfaces and each has a fanlike deflection because each of the reflection surfaces has its gradient, so that the ray projected on the electromagnetic radiation detector becomes clearer, increasing the measurement precision.

The reflection surfaces which are connected with each other shown in FIG. 6 are used as an example, and the present disclosure is not limited thereto. In practice, the reflection surfaces may be arc surfaces having different radians. In addition, widths of the reflection surfaces are not necessarily the same and can be adjusted according to the actual requirements.

Figure 7A:
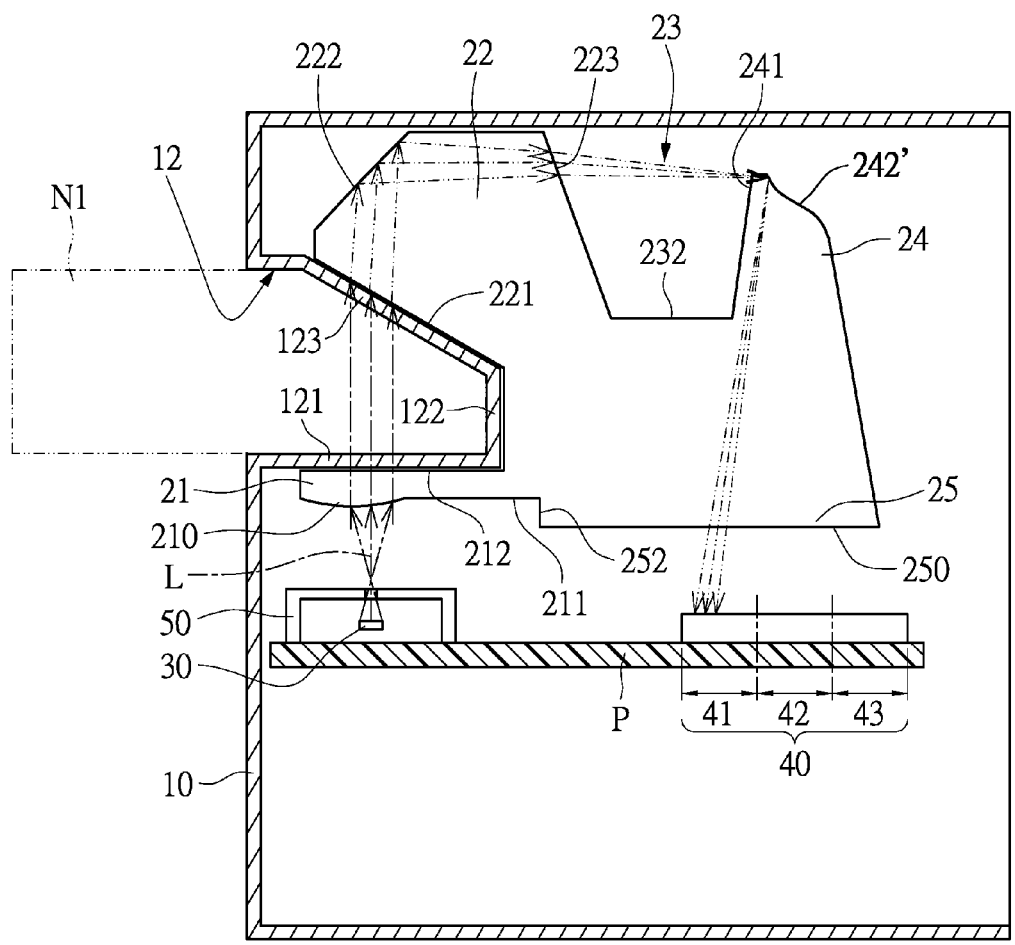
FIG. 7A is a schematic diagram illustrating the optical path of the solution having the first refraction index detected by the device for measuring solution concentration of the present disclosure.
Figure 7B:
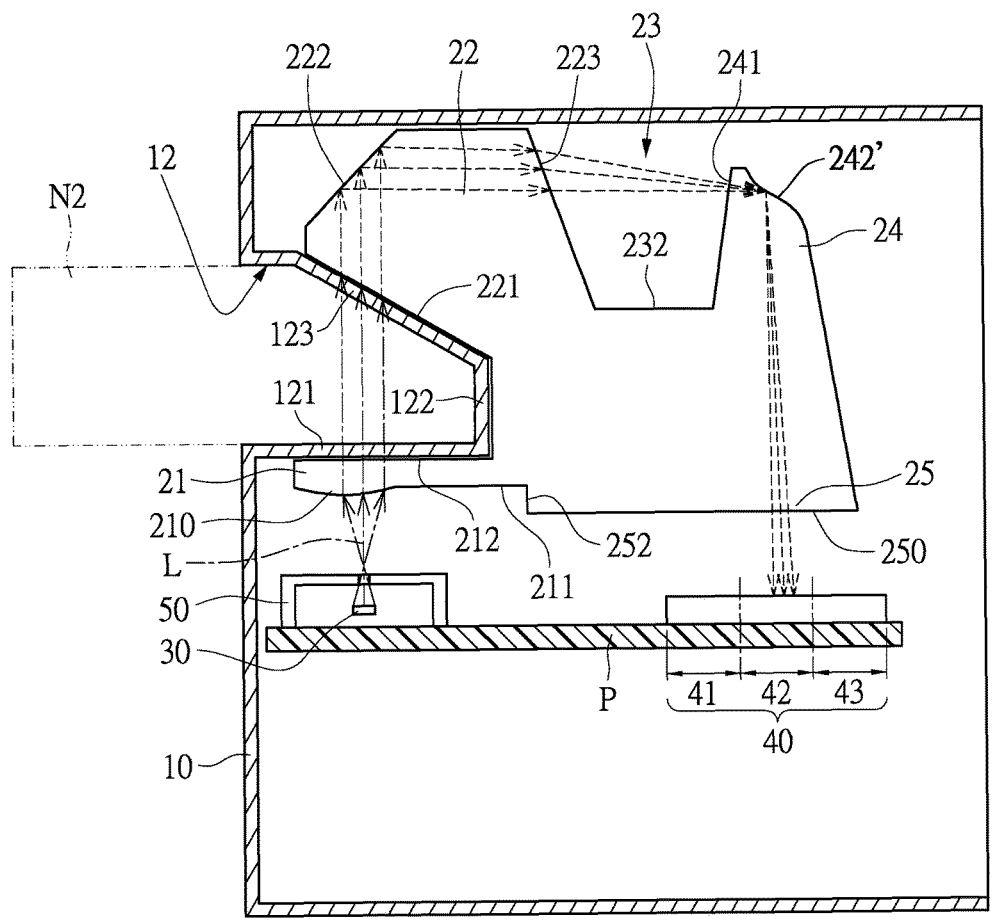
FIG. 7B is a schematic diagram illustrating the optical path of the solution having the second refraction index detected by the device for measuring solution concentration of the present disclosure.
Figure 7C:
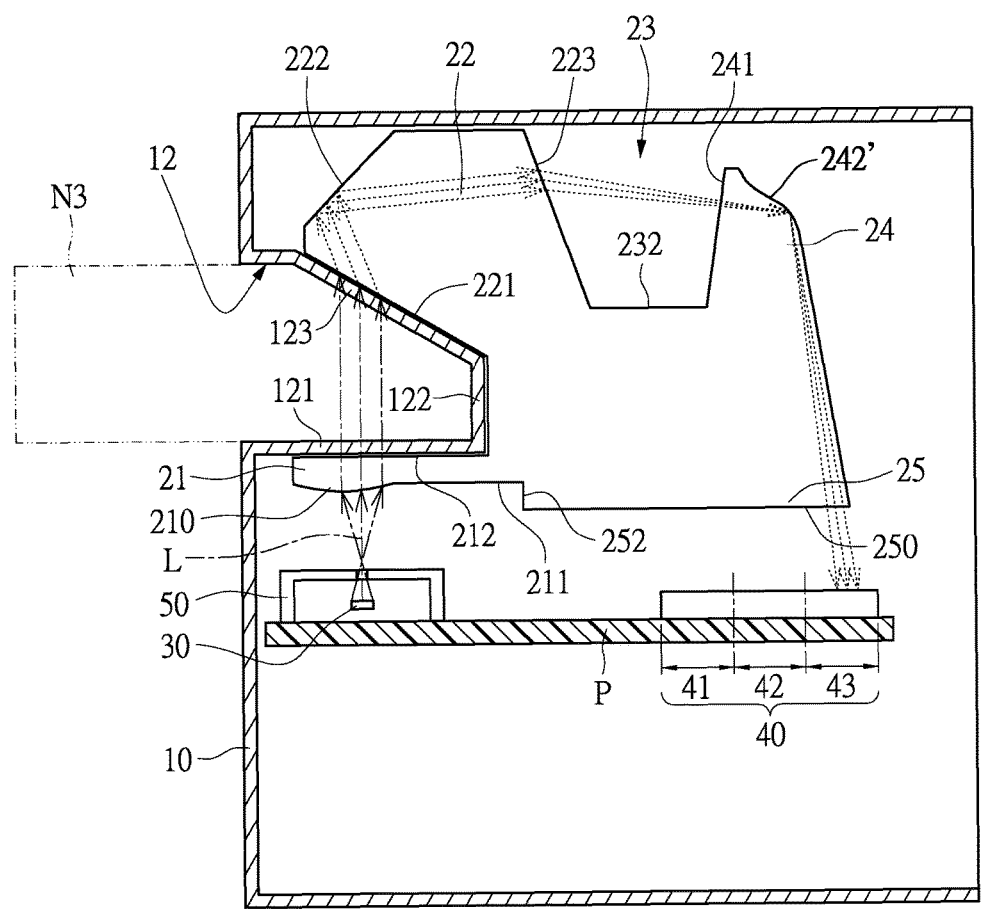
FIG. 7C is a schematic diagram illustrating the optical path of the solution having the third refraction index detected by the device for measuring solution concentration of the present disclosure.

Please refer to FIG. 7A to FIG. 7C which respectively illustrate optical paths of three solutions having different refraction indexes detected by the present disclosure, wherein the refraction index of the solution shown in FIG. 7A is greater than that in FIG. 7B, and the refraction index of the solution shown in FIG. 7B is greater than that in FIG. 7C. As shown in the figures, the device for measuring solution concentration is used to respectively measure the three solutions having different refraction indexes. Before reflecting off of the second total internal reflection face 242', the ray L is deflected, and after passing through the notch 23, the ray L has an obvious deflection. As shown in FIG. 5, when the present disclosure is used to measure solutions to be detected having different refraction indexes, the ray L at different positions of the second total internal reflection face is deflected again to increase the measurement precision. Alternatively, the ray L can be clearer to increase the measurement precision by cooperating with the embodiment shown in FIG. 6.

Figure 8:
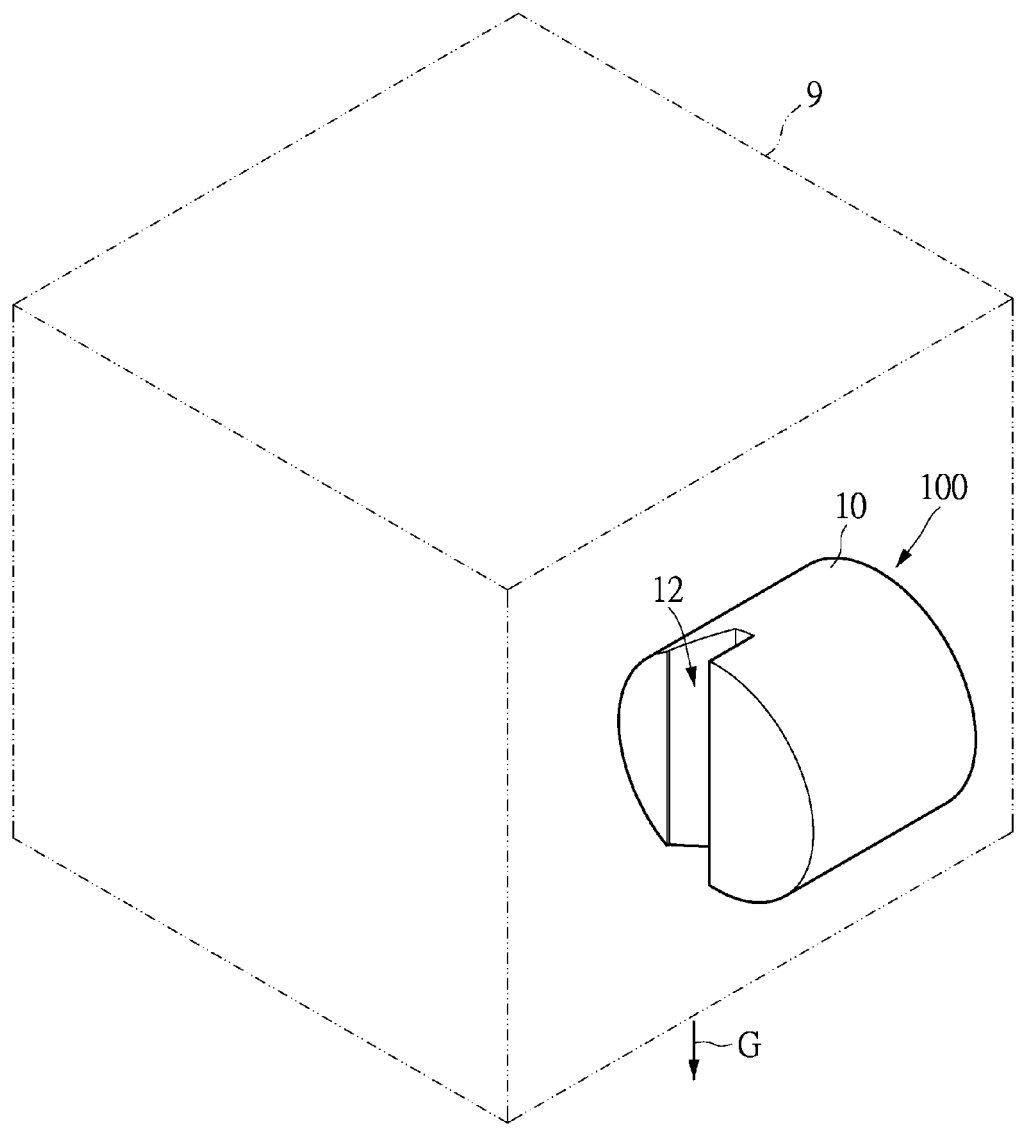
FIG. 8 is a three-dimensional diagram of the device for measuring solution concentration of the present disclosure disposed in a liquid container.

Please refer to FIG. 8 which is a three-dimensional diagram of the device for measuring solution concentration of the present disclosure disposed in a liquid container. In the present embodiment, the detecting part 12 of the housing 10 of the device for measuring solution concentration 100 has a shape of a ditch and is parallel to a direction of gravity G. In addition, the detecting part 12 has two open ends. Such a structure has the advantage that when the device for measuring solution concentration 100 is disposed in a liquid container 9, the solution to be detected in the liquid container 9 is freely passing the detecting part 12 without being deposited on the housing 10 so as to avoid covering the housing 10, so that the accuracy of measuring solution concentration is not affected. In addition, the detecting part 12 of the present embodiment is also beneficial in maintaining the measurement precision.

Figure 9:
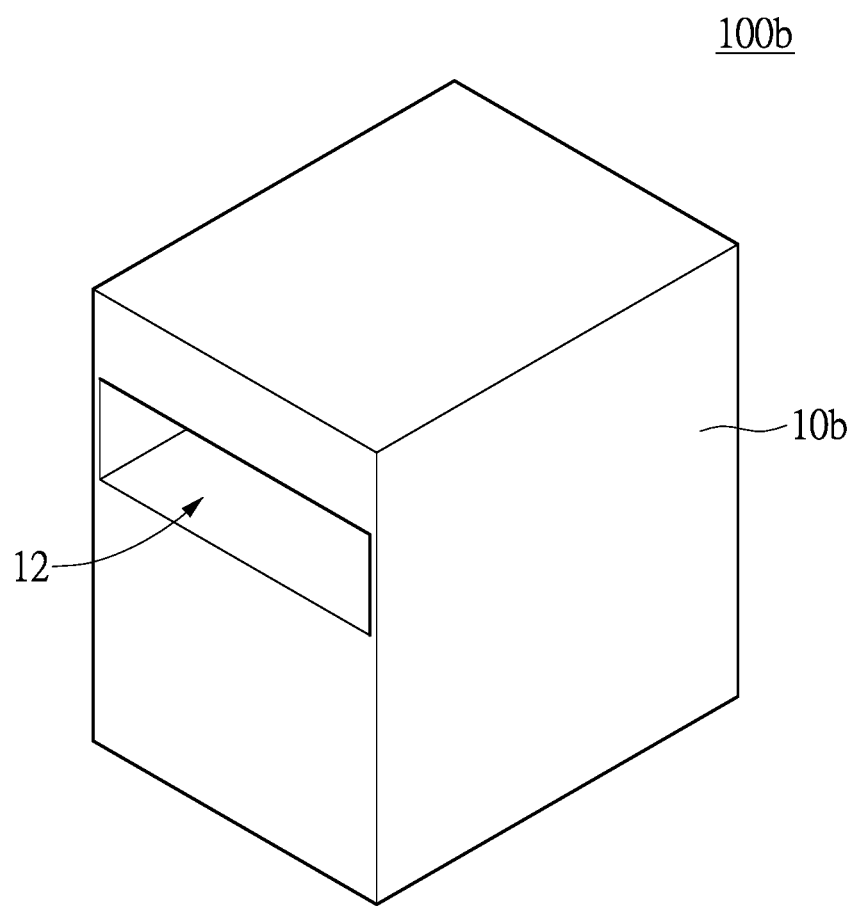
FIG. 9 is a three-dimensional diagram of the device for measuring solution concentration of the present disclosure disposed with another housing.
Figure 10:
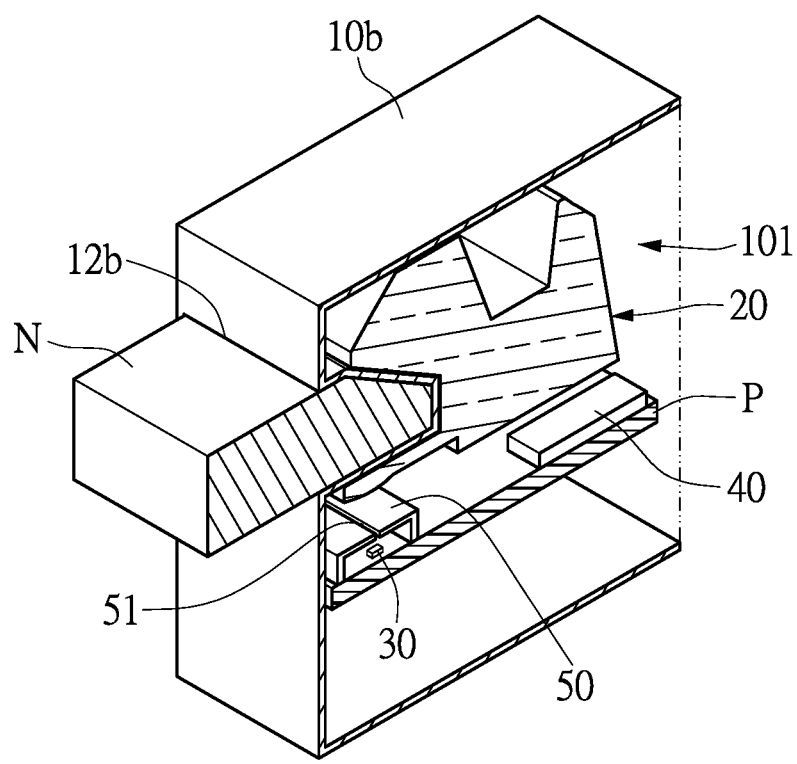
FIG. 10 is a sectional diagram of FIG. 9.

Please refer to FIG. 9 and FIG. 10, which are respectively a three-dimensional diagram of the device for measuring solution concentration of the present disclosure disposed with another housing and a sectional diagram of FIG. 9. The difference between the present disclosure and the former embodiment is that the housing 10b of the device for measuring solution concentration 100b of the present disclosure is a cube. The detecting part 12 is formed inwardly on the housing 10b. In the present embodiment, the housing 10b may be made of an electromagnetic radiation-transmittable material. The detecting part 12 has an upward opening, and the device for measuring solution concentration 100b is portable. For example, fluid samples can be injected in the detecting part 12 to be detected instantly. In addition, the components disposed in the device for measuring solution concentration 100b of the present disclosure are the same as in the former embodiment, which includes the housing 10; the catadioptric structure 20 received in the housing 10, the electromagnetic radiation emitter 30 and the electromagnetic radiation detector 40.

In summary, the device for measuring solution concentration of the present disclosure enables the ray L to have a refracted angle as it enters the solution to be detected, then it is totally internally reflected by two times to magnify the deflection angle, and the ray L is refracted by two times through the notch 23, wherein the present disclosure can magnify the deflection angle by several times to make the electromagnetic radiation detector 40 read the data more easily and accurately. In addition, the second total internal reflection face may be a convex lens-like shape or a free-form surface formed by connecting a plurality of micro-planes used to increase the measurement precision. The detecting part 12 of the present disclosure has a shape of a ditch and is parallel to a direction of gravity G, and has two open ends. Thus, the solution to be detected in the liquid container 9 freely passes the detecting part 12 without being deposited on the housing 10 so as to avoid covering the housing 10, so that the accuracy of the measuring solution concentration is not affected and the measurement precision is maintained.

As used herein, the term of "substantially", as applied to any number of modifications or errors caused by processing and manufacturing can change slightly, but a slight change or error does not change its nature.

The above-mentioned descriptions represent merely the exemplary embodiment of the present disclosure, without any intention to limit the scope of the present disclosure thereto. Various equivalent changes, alterations or modifications based on the claims of present disclosure are all consequently viewed as being embraced by the scope of the present disclosure.

What is claimed is:

1. A device for measuring solution concentration, comprising:
    a housing disposed with a closed accommodating space therein, and a detecting part formed inwardly on the housing used to detect a solution to be detected;
    a catadioptric structure received in the housing and comprising a ray entrance portion, a first total internal reflection part, a second total internal reflection part and a ray exit portion, wherein an accommodation part is formed between the ray entrance portion and the first total internal reflection part, the accommodating space has a shape corresponding to the detecting part, the detecting part is in the accommodating part, and the ray exit portion has a ray exit face;
    an electromagnetic radiation emitter disposed at one side of the ray entrance portion, wherein a ray emitted by the electromagnetic radiation emitter sequentially passes the ray entrance portion, the detecting part, the solution to be detected and the first total internal reflection part, and then the ray is totally internally reflected and converged to the second total internal reflection part, and is totally internally reflected again to pass the ray exit portion, and
    an electromagnetic radiation detector disposed at one side of the ray exit portion for receiving the ray from the ray exit portion, and the ray exit face facing the electromagnetic radiation detector.

2. The device for measuring solution concentration according to claim 1, further comprising a ray shield disposed between the electromagnetic radiation emitter and the ray entrance portion.

3. The device for measuring solution concentration according to claim 1, further comprising a circuit board, wherein the electromagnetic radiation emitter and the electromagnetic radiation detector are disposed on the same plane of the circuit board.

4. The device for measuring solution concentration according to claim 3, wherein the detecting part comprises a first ray-transmittable board, a second ray-transmittable board, and a connecting board for connecting the first ray-transmittable board and the second ray-transmittable board, wherein the first ray-transmittable board horizontally attaches a surface of the ray entrance portion and is parallel to the circuit board, and the second ray-transmittable board is inclined to the circuit board, wherein an acute angle is formed between the first ray-transmittable board and the second ray-transmittable board.

5. The device for measuring solution concentration according to claim 4, wherein the detecting part has a shape of a ditch and is parallel to a direction of gravity, and the detecting part has two open ends.

6. The device for measuring solution concentration according to claim 4, wherein the first total internal reflection part has a first entrance face attaching the second ray-transmittable board and a first total internal reflection face, and the first entrance face and the first total internal reflection face have an acute angle therebetween.

7. The device for measuring solution concentration according to claim 1, further comprising a notch formed between the first total internal reflection part and the second total internal reflection part, wherein the first total internal reflection part comprises a first exit face, the second total internal reflection part comprises a second entrance face, and the first exit face and the second entrance face are not parallel and define the notch together.

8. The device for measuring solution concentration according to claim 7, wherein the second total internal reflection part further comprises a second total internal reflection face which is a plane or a free-form surface.

9. The device for measuring solution concentration according to claim 1, wherein the second total internal reflection part has an upper reflection section, a main reflection section, and a lower reflection section, wherein the main reflection section is between the upper reflection section and the lower reflection section; the upper reflection section reflects the ray to a first area of the electromagnetic radiation detector, the main reflection section reflects the ray to a second area of the electromagnetic radiation detector and the lower reflection section reflects the ray to a third area of the electromagnetic radiation detector, wherein the second area is between the first area and the third area.

10. The device for measuring solution concentration according to claim 9, wherein the main reflection section has a reflection gradient that is smaller than a reflection gradient of the upper reflection section, and the lower reflection section has a reflection gradient that is smaller than a reflection gradient of the main reflection section.

11. The device for measuring solution concentration according to claim 1, wherein the second total internal reflection part has a second total internal reflection face comprising a first reflection surface, a second reflection surface, and a third reflection surface; and a first included angle, a second included angle and a third included angle are respectively formed between the first reflection surface, the second reflection surface and the third reflection surface and an imaginary line perpendicular to the ray exit face, wherein the first included angle<the second included angle<the third included angle.

12. The device for measuring solution concentration according to claim 11, wherein each of the reflection surfaces has an arc surface forming the free-form surface, and the free-form surface is used to focus light.

13. A device for measuring solution concentration, comprising:
    a housing having a closed accommodating space formed therein, and a detecting part formed inwardly on the housing for receiving a solution to be detected,
    a catadioptric structure received in the housing, and comprising a ray entrance portion, a first total internal reflection part, a second total internal reflection part and a ray exit portion, wherein an accommodation part is formed between the ray entrance portion and the first total internal reflection part, the accommodating part has a shape corresponding to the detecting part, the detecting part is in the accommodating part, wherein the detecting part has a shape of a ditch and is parallel to a direction of gravity, and has two open ends, and the ray exit portion has a ray exit face;

an electromagnetic radiation emitter disposed at one side of the ray entrance portion, a ray emitted by the electromagnetic radiation emitter sequentially passing the ray entrance portion, the detecting part, the solution to be detected and the first total internal reflection part, and then the ray totally internally reflected and converged to the second total internal reflection part and totally internally reflected again to pass the ray exit portion; and an electromagnetic radiation detector disposed at one side of the ray exit portion for receiving the ray from the ray exit portion, and the ray exit face facing the electromagnetic radiation detector.

14. The device for measuring solution concentration according to claim 13, wherein the second total internal reflection part further comprises a second total internal reflection face which is a non-planar surface or a free-form surface.

15. The device for measuring solution concentration according to claim 14, wherein the second total internal reflection face has a plurality of micro-planes, and one of the micro-planes which is adjacent to the notch has a greater gradient than one of the micro-planes which is far from the notch, wherein the gradient is relative to the ray exit face.

16. The device for measuring solution concentration according to claim 14, wherein the second total internal reflection part has an upper reflection section, a main reflection section, and a lower reflection section, wherein the main reflection section is between the upper reflection section and the lower reflection section; the upper reflection section reflects the ray to a first area of the electromagnetic radiation detector, the main reflection section reflects the ray to a second area of the electromagnetic radiation detector and the lower reflection section reflects the ray to a third area of the electromagnetic radiation detector, wherein the second area is between the first area and the third area.

17. The device for measuring solution concentration according to claim 14, wherein the second total internal reflection face has a plurality of reflection surfaces, and each of the reflection surfaces has an arc surface forming the free-form surface, and the free-form surface is used to focus light.

* * * * *